United States Patent [19]

Ciraldo et al.

[11] Patent Number: 4,623,339

[45] Date of Patent: Nov. 18, 1986

[54] PRECIOUS BABY DIAPER

[76] Inventors: Joann Ciraldo; Joseph R. Ciraldo; George Spector, all of 233 Broadway Rm 3615, New York, N.Y. 10007

[21] Appl. No.: 765,805

[22] Filed: Aug. 15, 1985

[51] Int. Cl.⁴ .............................................. A61F 13/16
[52] U.S. Cl. ..................................... 604/359; 604/360
[58] Field of Search ............... 604/385, 359, 394, 393, 604/358, 360

[56] References Cited

U.S. PATENT DOCUMENTS

| | | | |
|---|---|---|---|
| 3,585,998 | 6/1971 | Hayford et al. | 604/359 |
| 3,875,942 | 4/1975 | Roberts et al. | 604/359 |
| 4,051,854 | 10/1977 | Aaron | 604/394 |
| 4,221,221 | 9/1980 | Ehrlich | 604/385 |

Primary Examiner—John D. Yasko

[57] ABSTRACT

An improved disposable diaper is provided and consists of a pouch on inner surface of the interior liner at crotch portion of the diaper. The pouch contains lotion/ointment therein and has a plurality of minute perforations. When an adhesive strip is removed from the perforations the lotion/ointment will come out onto skin of a baby when the diaper is placed onto the baby.

4 Claims, 7 Drawing Figures

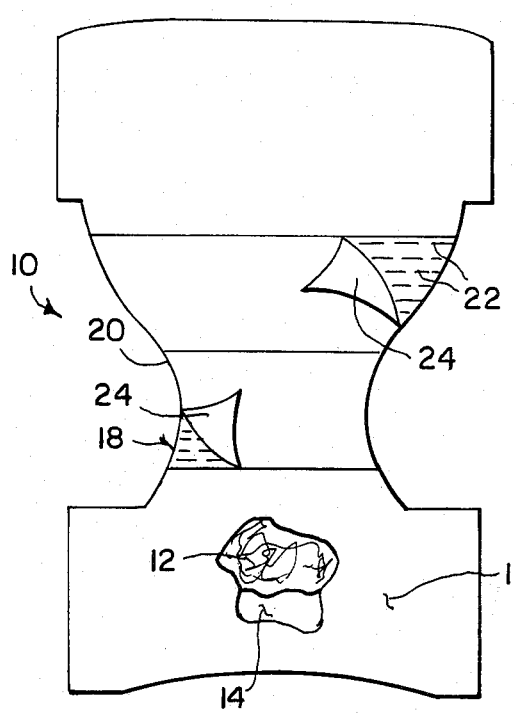
Fig. 1
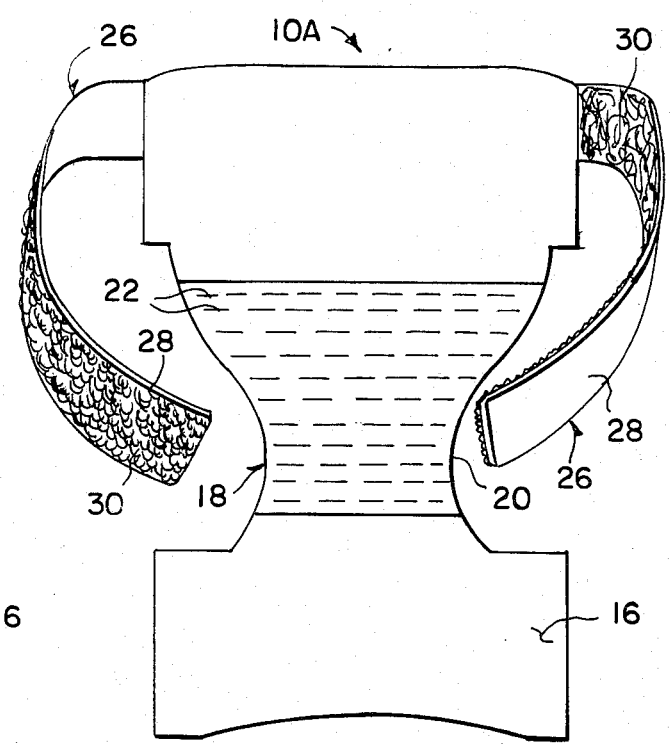
Fig. 2
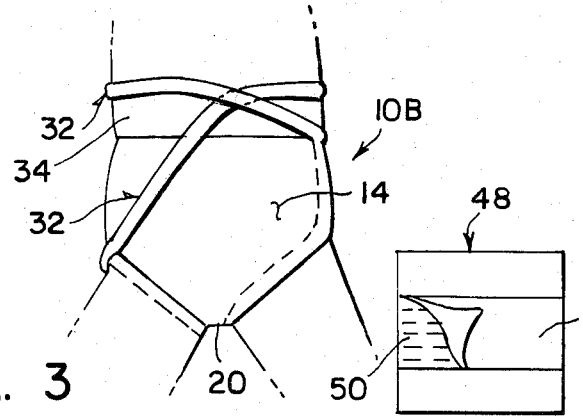
Fig. 3
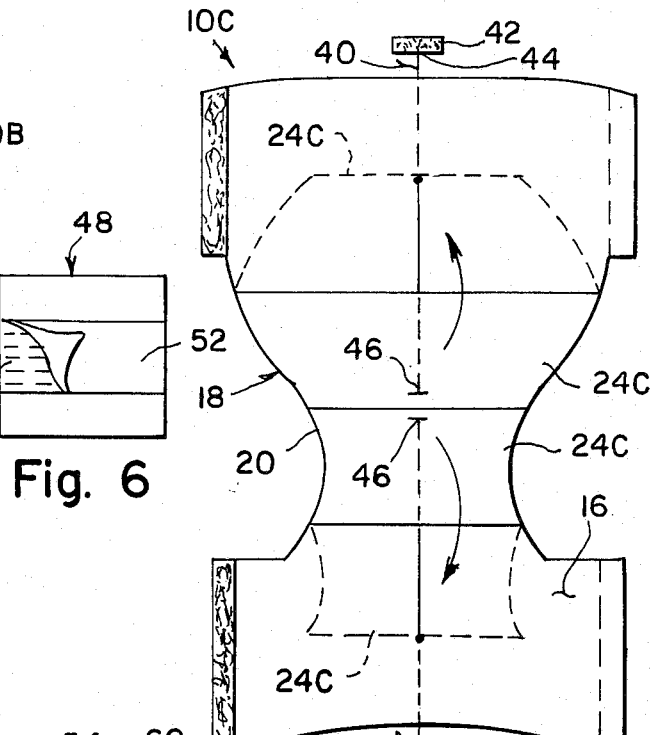
Fig. 5
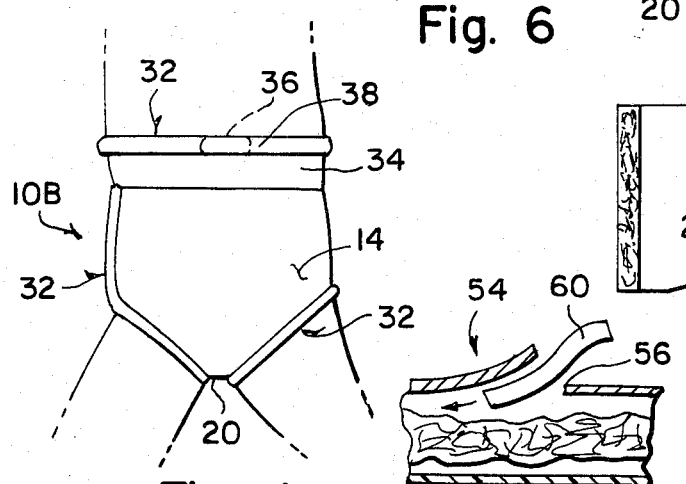
Fig. 4
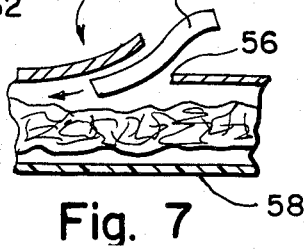
Fig. 6
Fig. 7

PRECIOUS BABY DIAPER

BACKGROUND OF THE INVENTION

The instant invention relates generally to disposable diapers and more specifically it relates to an improved disposable diaper with a lotion/ointment pouch.

Numerous disposable diapers have been provided in prior art that are adapted to be impregnated with lotions and medications to counteract irritation of the infants skin due to contact with body wastes. For example, U.S. Pat. Nos. 2,627,858; 3,585,998 and 3,964,486 all are illustrative of such prior art. While these units may be suitable for the particular purpose to which they address, they would not be as suitable for the purpose of the present invention, as heretofore described.

SUMMARY OF THE INVENTION

A principle object of the present invention is to provide an improved disposable diaper with a lotion/ointment pouch that overcomes the shortcomings of the prior art devices.

Another object is to provide an improved disposable diaper with a lotion/ointment pouch whereby the antiseptic lotion/ointment will pour out on the baby making the baby more comfortably fresh and germ safe.

An additional object is to provide an improved disposable diaper with a lotion/ointment pouch whereby the pouch can be a separate unit which can be inserted in a regular disposable diaper and used as a liner filler.

A further object is to provide an improved disposable diaper with a lotion/ointment pouch that is simple and easy to use.

A still further object is to provide an improved disposable diaper with a lotion/ointment pouch that is economical in cost to manufacture.

Further objects of the invention will appear as the description proceeds.

To the accomplishment of the above and related objects, this Invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a plan view of one form of the invention being a disposable diaper with a built in pouch in the crotch portion.

FIG. 2 is a plan view of another form of the invention having a pair of belt extensions for securing to baby.

FIG. 3 is a front view of still another form of the invention having a pair of elongated strip covers and belts which protect the pouch and also are used to secure the diaper to baby.

FIG. 4 is a rear view of the diaper in FIG. 3.

FIG. 5 is a plan view of yet another form of the invention having a pair of pull strings with velcro retainers, the strings open the adhesive strips while the retainers hold the string secured to the diaper when opened.

FIG. 6 is a plan view of another form of the invention being a diaper pad with a pouch which can be inserted in a regular disposable diaper and used as a liner filler.

FIG. 7 is a cross sectional view of another form of the invention wherein a regular diposable diaper contains a slit in the crotch portion so that an insert with lotion/ointment can be placed therein.

DETAILED DESCRIPTION OF THE PREFERRED EMBODIMENTS

Turning now descriptively to the drawings, in which similar reference characters denote similar elements throughout the several views, FIG. 1 illustrates an improved disposable diaper 10 that has a centrally located absorbent, porous, fibrous core section 12; a moisture-impermeable exterior liner 14 positioned on one side thereof and, a moisture permeable interior liner 16 positioned on other side thereof.

The improvement consists of a pouch 18 secured on inner surface of the interior liner 16 at crotch portion 20 of the diaper 10. The pouch 18 contains lotion/ointment therein and has a plurality of minute perforations 22. Adhesive strip or strips 24 are for covering the perforations 22. When the adhesive strip or strips 24 are removed, the lotion/ointment will come out onto the skin of a baby when the diaper 10 is placed onto the baby.

As shown in FIG. 2 the improved disposable diaper 10A further contains a pair of belt extensions 26. Each belt extension 26 is affixed to the diaper 10A. The free ends 28 of the belt extensions 26 have velcro fasteners 30 for fastening the free ends 28 together for securing the diaper 10A when the diaper is placed onto the baby, other types of fasteners (not shown) such as snaps, buckles etc. can be used.

FIGS. 3 and 4 show elongated strip cover belts 32. The elongated adhesive strip belts 32 are used to both protect the pouch 18 and secure the diaper 10B when the diaper is placed onto the baby. The belts 32 extend from the crotch portion 20 wrap around the waist 34 of the baby and have velcro fasteners 36 at the free ends 38.

FIG. 5 shows a disposable diaper 10C further containing a pair of strings 40. Each string has a fastener retainer 42 at free end 44 and connected at other end 46 to one of the adhesive strips 24C. When the diaper 10C is placed onto the baby the strings 40 can be pulled to open the adhesive strips 24C and expose the minute perforations 22 while the fastener retainers 42 can hold the strips 40 secured to the diaper 10C.

FIG. 6 shows another form of the invention being a diaper pad 48 made out of the same material as the disposable diaper. The diaper pad 48 has a pouch 50 with an adhesive strip 52 and being of the same material as pouch 18. The diaper pad 48 can be inserted in a regular disposable diaper (not shown) and used as a liner filler.

FIG. 7 is a cross section of a regular disposable diaper 54 having a slit 56 in the crotch portion 58 so that an insert 60 with the lotion/ointment can be placed therein. The lotion/ointment will be spread within the diaper 54.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An improved disposable diaper of the type having a centrally located absorbent, porous, fibrous core section, a moisture impermeable exterior liner positioned on one side thereof and a moisture permeable interior liner positioned on other side thereof wherein the improvement comprises:
  (a) a pouch secured on inner surface of said interior liner at a crotch portion of said diaper, said crotch portion having opposite sides, said pouch containing lotion/ointment therein and having a plurality of minute perforations; and
  (b) an adhesive strip for covering said perforations so that when said adhesive strip is removed said lotion/ointment will come out onto skin of a baby when said diaper is placed onto said baby;
  (c) means secured to said diaper manually actuated to remove said adhesive strip.

2. An improved disposable diaper comprising:
a centrally located absorbent, porous, fibrous core section, a moisture impermeable exterior liner positioned on one side thereof and a moisture permeable interior liner positioned on other side thereof wherein the improvement comprises:
  (a) a pouch secured on inner surface of said interior liner at a crotch portion of said diaper said crotch portion having opposite sides, said pouch containing lotion/ointment therein and having a plurality of minute perforations;
  (b) an adhesive strip for covering said perforations so that when said adhesive strip is removed said lotion/ointment will come out onto skin of a baby when said diaper is placed onto said baby;
  (c) a pair of belt extensions, each belt extension affixed to said diaper and extend from opposite sides of said crotch to cross wrap around the waist of the baby terminating in ends;
  (d) means for fastening said ends together for securing said diaper, whereby said belt has portions sealingly disposed along the baby's body adjacent said crotch portion.

3. An improved disposable diaper as recited in claim 1, wherein said means comprise a string with a fastener at free end and connected at other end to said adhesive strip so that when said diaper is placed onto said baby said string can be pulled to open said adhesive strip and expose said minute perforations while said fastener can hold said string secured to said diaper.

4. A diaper as in claim 1, wherein said pouch is removeable and said diaper has a slit in the crotch portion to insert and remove pouches.

* * * * *